United States Patent
Balya et al.

(10) Patent No.: US 9,844,579 B2
(45) Date of Patent: Dec. 19, 2017

(54) THERAPEUTICAL TOOLS AND METHODS FOR TREATING BLINDNESS

(71) Applicant: FRIEDRICH MIESCHER INSTITUTE FOR BIOMEDICAL RESEARCH, Basel (CH)

(72) Inventors: David Balya, Basel (CH); Volker Busskamp, Loerrach (DE); Pamela Lagali, Basel (CH); Botond Roska, Oberwil (CH)

(73) Assignee: Friedrich Miescher Institute for Biomedical Research, Basel (CH)

( * ) Notice: Subject to any disclaimer, the term of this patent is extended or adjusted under 35 U.S.C. 154(b) by 0 days.

(21) Appl. No.: 15/005,302

(22) Filed: Jan. 25, 2016

(65) Prior Publication Data

US 2016/0250282 A1    Sep. 1, 2016

Related U.S. Application Data

(63) Continuation of application No. 13/300,045, filed on Nov. 18, 2011, now abandoned, which is a continuation of application No. 12/988,336, filed as application No. PCT/EP2009/054562 on Apr. 16, 2006, now abandoned.

(30) Foreign Application Priority Data

Apr. 18, 2008  (EP) ..................... 08154828
May 9, 2008    (EP) ..................... 08155942

(51) Int. Cl.
| | |
|---|---|
| A61K 48/00 | (2006.01) |
| C12N 15/12 | (2006.01) |
| C07H 21/00 | (2006.01) |
| A61K 38/16 | (2006.01) |
| C07K 14/215 | (2006.01) |
| A61K 38/00 | (2006.01) |

(52) U.S. Cl.
CPC .......... *A61K 38/164* (2013.01); *A61K 48/005* (2013.01); *A61K 48/0075* (2013.01); *C07K 14/215* (2013.01); *A61K 38/00* (2013.01); *C12N 2799/025* (2013.01); *C12N 2830/008* (2013.01)

(58) Field of Classification Search
None
See application file for complete search history.

(56) References Cited

U.S. PATENT DOCUMENTS

2012/0258530 A1   10/2012   Balya et al.

FOREIGN PATENT DOCUMENTS

| WO | 2007/131180 A2 | 11/2007 | |
|---|---|---|---|
| WO | 2008/022772 A1 | 2/2008 | |
| WO | WO 2008/137066 | * 11/2008 | ............. A61K 9/127 |

OTHER PUBLICATIONS

Han et al; "Multiple-Color Optical Activation, Silencing, and Desynchronization of Neural Activity, with Single-Spike Temporal Resolution"; PLoS One 2(3):e299 (2007).
Häusser et al; "Controlling Neural Circuits with Light"; Nature 446(7136):617-619 (2007).
Herlitze et al; "New Optical Tools for Controlling Neuronal Activity"; Current Opinion in Neurobiology 17(1):87-94 (2007).
Lanyi et al; "The Primary structure of a Halorhodopsin from *Natronobacterium pharaonis*. Structural, Functional, and Evolutionary Implications for Bacterial Rhodopsins and Halorhodopsins"; Journal of Biological Chemistry 265(3):1253-1260 (1990).
Mukohata et al; "Halobacterial Rhodopsins"; Journal of Biochemistry 125(4):649-657 (1999).
Zhang et al; "Circuit-breakers: optical technologies for probing neural signals and systems"; Nature Reviews Neuroscience 8(8):577-581 (2007).
Zhang et al; "Multimodal fast optical interrogation of neural circuitry"; Nature 446(7136):633-639 (2007).
Zhang et al; "Red-shifted optogenetic excitation: a tool for fast neural control derived from *Volvox carteri*"; Nature Neuroscience 11(6):631-633 (2008).

* cited by examiner

Primary Examiner — Scott Long
Assistant Examiner — Arthur S Leonard
(74) Attorney, Agent, or Firm — Sherwin Y. Chan

(57) ABSTRACT

The present inventions relates to the use of an isolated nucleic acid molecule comprising a nucleotide sequence coding for a hyperpolarizing light-gated ion channel or pump gene from an archeon or for a light-active fragment of said gene, or the nucleotide sequence complementary to said nucleotide sequence, for treating or ameliorating blindness. The light-gated ion channel or pump gene can be a halorhodopsin gene.

18 Claims, 1 Drawing Sheet

THERAPEUTICAL TOOLS AND METHODS FOR TREATING BLINDNESS

FIELD OF THE INVENTION

The present invention relates to methods of treating blindness. The present invention also relates to constructs for use in treating blindness, as well as their use in the manufacture of a medicament for treating blindness.

BACKGROUND OF THE INVENTION

Blindness is a major health problem that disables millions of people worldwide. The most common cause of blindness is the disfunction of the retina. The three most common forms of retinal blindness are retinitis pigmentosa (RP), macular deneneration (MD) and glaucoma (G). In RP and MD the primary problem is the degeneration of photoreceptors and the consequent loss of photosensitivity. There is thus a need to be able to obviate the problems associated with such degeneration of photoreceptors.

One approach has been to develop a retinal prosthesis, a "seeing eye" chip with as many as 1,000 tiny electrodes to be implanted in the eye. This would have the potential to help people who have lost their sight to regain enough vision to function independently, but the numbers of electrodes is simply insufficient to provide a high degree or level of sight to be obtained. Moreover, there are problems associated with inserting foreign bodies into the eye. Recently a number of genes has been isolated and/or manipulated that when expressed can make cells light sensitive. In some cases additional non-genetic factors are also needed to make cells light sensitive.

One proposal by Eli in 2001 was to use the chlorophyll-containing proteins in spinach to treat vision loss. These proteins give off a small electrical voltage after capturing the energy of incoming photons of light. Although, the research has shown that photosystem I reaction centres can be incorporated into a liposome and are shown to be functional, in that it produces the experimental equivalent of a voltage when light is shone on it, hitherto this has not been shown to work in a retinal cell.

Other work by neurobiologist Richard Kramer at UC Berkeley has looked at re-engineering a potassium channel to be responsive to light rather than voltage, in order to allow insertion of a light activated switch into brain cells normally insensitive to light. However, the channel has to be mutated so that it always stays open and a chemical "plug", attached to the channel, which is sensitive to light such that when lit with long-wavelength UV light, the plug is released from the channel, letting potassium out of the channel. Light of a longer wavelength causes the plug to insert back into the channel and stop release of potassium. It will be appreciated however, that such a system is extremely complex and problems are likely to arise if the channel is delivered to the wrong type of retinal cells.

Bi et al., (Neuron, 50, 2006, p 23-33) discloses the use of microbial-type rhodopsin to restore visual responses in mice with photoreceptor degeneration. However, the expression of the rhodopsin gene is likely to have occurred in a variety of types of cell in the eye which is potentially undesirable and/or problematic. It also appears that the threshold light intensity required for producing responses is much higher than for normal rod and cone photoreceptors, but there is no teaching of how this may be addressed in, for example, low light environments.

An alternative method has been described by some of the present inventors in WO-A-2008/022772, wherein e.g. channelrhodopsin-2 is targeted to e.g. ON-cells. This method has however the disadvantage of being sub-optimal with OFF-cells.

It is amongst the objects of the present invention to obviate and/or mitigate at least one of the aforementioned disadvantages.

It is also an object of the present invention to provide a system suitable for use in preventing and/or treating blindness in a subject.

SUMMARY OF THE INVENTION

To address this need, the present inventors investigated the capacity of a phylogenetically ancient hyperpolarizing light sensor, such as the halorhodopsin from the archeon (archeabacteria) *Natronomas pharaonis* (NpHR), specifically expressed in rod and cone photoreceptors for its capacity to restore vision in an experimental model for blindness.

Surprisingly, the inventors realized that this receptor on itself could, when introduced into rod and cone photoreceptors, stimulate both the ON- and the OFF-system, and restore some vision on itself, i.e. without the need of any of the numerous other light transduction cascade components usually found in rod and cone photoreceptors The present invention therefore encompasses an isolated nucleic acid molecule comprising a nucleotide sequence coding for a hyperpolarizing light-gated ion channel or pump gene from an archeon or for a light-active fragment of said gene, or the nucleotide sequence complementary to said nucleotide sequence, for use in treating or ameliorating blindness. Said light-gated ion channel or pump gene can be halorhodopsin gene, for instance the halorhodopsin gene from *Natronomas pharaonis* (NpHR).

The isolated nucleic acid molecule of the invention can be used by administration and expression in at least one of cones, rods, horizontal cells, rod bipolar cells, ON-cone bipolar cells, OFF-cone bipolar cells, amacrine cells, ganglion cells. Therefore, the isolated nucleic acid molecule of the invention can comprise a cell specific promoter, for instance human rhodopsin promoter, human red opsin promoter the Grm6 promoter controlling the expression of the light-gated ion channel or pump gene.

Moreover, the isolated nucleic acid molecule of can be used, simultaneously or sequentially, together with a depolarizing light-gated ion channel gene, for example a channelrhodopsin, for instance channelrhodopsin-2. Moreover, the depolarizing light-gated ion channel gene can be under the control of human rhodopsin promoter, human red opsin promoter and the Grm6 promoter.

The present invention also encompasses an isolated nucleic acid molecule useful for treating blindness comprising a nucleic acid sequence coding for a hyperpolarizing light-gated ion channel or pump gene and a nucleic acid sequence coding for a depolarizing light-gated ion channel or pump gene. An embodiment thereof is an isolated nucleic acid molecule wherein said hyperpolarizing light-gated ion channel or pump gene is halorhodopsin, for instance the halorhodopsin gene from *Natronomas pharaonis* (NpHR), and said a depolarizing light-gated ion channel gene is a channelrhodopsin, for instance channelrhodopsin-2. In this case, the hyperpolarizing light-gated ion channel or pump and the depolarizing light-gated ion channel can be encoded in such a way that a fusion protein is formed upon expression. Moreover, both genes can be, either commonly or independently, under the control of a promoter chosen from the group of human rhodopsin promoter, human red opsin promoter and the Grm6 promoter.

The present invention further encompasses a recombinant vector comprising a nucleic acid of the invention or a host cell comprising said vector.

In addition, the present invention also encompasses a kit comprising an isolated nucleic molecule of the invention, a recombinant vector comprising said molecule or a host cell comprising said vector.

DETAILED DESCRIPTION OF THE INVENTION

Figure 1:
FIG. 1: AAV2-Rho-NpHR-EYFP genomic vector

To address this need, the present inventors investigated the capacity of a phylogenetically ancient hyperpolarizing light sensor, such as the halorhodopsin from the archeon (archeabacteria) *Natronomas pharaonis* (NpHR), specifically expressed in rod and cone photoreceptors for its capacity to restore vision in an experimental model for blindness. Surprisingly, the inventors realized that this receptor on itself could, when introduced into rod and cone photoreceptors, stimulate both the ON- and the OFF-system, and restore some vision on itself, i.e. without the need of any of the numerous other light transduction cascade components usually found in rod and cone photoreceptors The present invention therefore encompasses an isolated nucleic acid molecule comprising a nucleotide sequence coding for a hyperpolarizing light-gated ion channel or pump gene from an archeon or for a light-active fragment of said gene, or the nucleotide sequence complementary to said nucleotide sequence, for use in treating or ameliorating blindness. Said light-gated ion channel or pump gene can be halorhodopsin gene, for instance the halorhodopsin gene from *Natronomas pharaonis* (NpHR).

The isolated nucleic acid molecule of the invention can be used by administration and expression in at least one of cones, rods, horizontal cells, rod bipolar cells, ON-cone bipolar cells, OFF-cone bipolar cells, amacrine cells, ganglion cells. Therefore, the isolated nucleic acid molecule of the invention can comprise a cell specific promoter, for instance human rhodopsin promoter, human red opsin promoter the Grm6 promoter controlling the expression of the light-gated ion channel or pump gene.

Moreover, the isolated nucleic acid molecule of can be used, simultaneously or sequentially, together with a depolarizing light-gated ion channel gene, for example a channelrhodopsin, for instance channelrhodopsin-2. Moreover, the depolarizing light-gated ion channel gene can be under the control of human rhodopsin promoter, human red opsin promoter and the Grm6 promoter.

The present invention also encompasses an isolated nucleic acid molecule useful for treating blindness comprising a nucleic acid sequence coding for a hyperpolarizing light-gated ion channel or pump gene and a nucleic acid sequence coding for a depolarizing light-gated ion channel or pump gene. An embodiment thereof is an isolated nucleic acid molecule wherein said hyperpolarizing light-gated ion channel or pump gene is halorhodopsin, for instance the halorhodopsin gene from *Natronomas pharaonis* (NpHR), and said a depolarizing light-gated ion channel gene is a channelrhodopsin, for instance channelrhodopsin-2. In this case, the hyperpolarizing light-gated ion channel or pump and the depolarizing light-gated ion channel can be encoded in such a way that a fusion protein is formed upon expression. Moreover, both genes can be, either commonly or independently, under the control of a promoter chosen from the group of human rhodopsin promoter, human red opsin promoter and the Grm6 promoter.

The present invention further encompasses a recombinant vector comprising a nucleic acid of the invention or a host cell comprising said vector.

In addition, the present invention also encompasses a kit comprising an isolated nucleic molecule of the invention, a recombinant vector comprising said molecule or a host cell comprising said vector.

Moreover, the present invention also encompasses method of treating blindness using the isolated nucleic acid molecules or vectors of the invention.

Compositions comprising the nucleic acid molecules of the invention are also encompassed by the present invention. Said compositions can be pharmaceutically acceptable compositions.

Moreover, the nucleic acid molecules of the invention can be used to manufacture medicaments and/or to treat patients. Hence, the present invention also encompasses methods of treatment using the nucleic acid molecules of the invention It is to be understood that the medicament is generally used therapeutically, but it may be used in a prophylactic sense, when a subject has been identified as being likely to suffer from blindness, but actual vision loss has not yet occurred or has only minimally occurred.

By "blindness" is meant total or partial loss of vision. Typically the medicament may be used to treat blindness associated with macular degeneration, glaucoma and/or retinitis pigmentosa. However, it is to be appreciated that any disease or condition which leads to degeneration or non-functioning of photoreceptors in the eye may be treated using the medicament. Moreover, without wishing to be bound by theory, it is believed that the present invention will be particularly effective for curing blindness at early stages of retinal degeneration (rd) when photoreceptor function is lost but the photoreceptor-to-bipolar synapse may still be intact.

An "active fragment of the light-gated ion channel or pump" is a fragment which when expressed generates a polypeptide which is still capable of functioning as a light capturing molecule which causes a subsequent flow of ions into or out of the cell in which the channel is located and a consequent change in voltage.

By "hyperpolarisation" is meant to decrease the membrane potential of a cell. By "Depolarisation" is meant to increase the membrane potential of a cell.

It will be appreciated that the present invention also extends to methods of treating prophylactically or therapeutically blindness by administering to a patient suffering or predisposed to developing blindness, a DNA construct according to the invention comprising a light-gated ion channel or pump gene sequence or active fragment thereof, which gene sequence or fragment thereof is capable of expressing one or more copies of the light-gated ion channel or pumpprotein in a retinal cell, whereby expression of said one or more copies of the light-gated ion channel or pump protein render the cell photosensitive so as to enable treatment or amelioration of blindness.

Typically, the light-gated ion channel or pump gene sequence of the invention or fragment thereof may be administered to a subject in the form of a recombinant molecule comprising said light-gated ion channel gene sequence or active fragment under appropriate transcriptional/translational controls to allow expression of said light-gated ion channel or pump protein when administered to retinal cells of a subject. It will be appreciated that the light-gated ion channel or pump sequence or fragment may be under control of a suitable promoter, such as a constitutive and/or controllable promoter.

The present invention also therefore provides a recombinant molecule of the invention comprising a light-gated ion channel or pump gene sequence or active fragment thereof for use in therapy. The recombinant molecule may be in the form of a plasmid, phagemid or viral vector. Furthermore, recombinantly expressed, or chemically synthesised light-gated ion channel or pump protein, or functionally important fragments thereof, may be produced and applied to the eye via a suitable ointment or other pharmaceutical vehicle, as a treatment or prophylactic measure for treating said aforementioned diseases.

Many different viral and non-viral vectors and methods of their delivery, for use in gene therapy, are known, such as adenovirus vectors, adeno-associated virus vectors, retrovirus vectors, lentiviral vectors, herpes virus vectors, liposomes, naked DNA administration and the like. A detailed review of possible techniques for transforming genes into desired cells of the eye is taught by Wright (Br J Ophthalmol, 1997; 81: 620-622) which is incorporated herein by reference. Moreover, it may also be possible to use encapsulated cell technology as developed by Neurotech, for example.

The light-gated ion channel or pump gene is a halorhodopsin gene and can be if desired combined with a rhodopsin, such as a rhodopsin from a microorganism, such as a unicellular alga, typically from the species *Chlamydononas*, especially *Chlamydomonas reinhardtii*. A preferred rhodopsin is Channelrhodopsin-2 (ChR2) which is a light gated cation channel from *C. reinhardtii*, see for example, Boyden et al 2005 (Nature Neuroscience, 8, 9; 1263-1268) and WO-A-2003/084994.

Preferably the cells to which the medicament or vector are to be administered, and in which the gene is to be expressed are rod bipolar cells, ON cone bipolar cells, OFF cone bipolar cells, horizontal cells, amacrine cells and ganglion cells. Moreover, the photoreceptor cells (rod and cones) themselves which have lost photosensitivity, but which are not "dead" can be used to express the light-gated ion channel or pump gene. Moreover expression of the light-gated ion channel or pump gene in photoreceptors may serve to prevent or show down degeneration.

It is understood that it is preferable that expression of the light-gated ion channel gene of the invention is controlled by way of a cell specific promoter. Thus a cell specific promoter may be used to ensure that the light-gated ion channel gene is only expressed in a specific cell type. For example, the mGluR6 promoter (Ueda et al, J Neurosci. 1997 May 1; 17(9):3014-23) may be employed to control expression in ON-bipolar cells.

Once expressed in an appropriate retinal cell, the light-gated ion channel or pump protein inserts within the plasma membrane of the cell, rendering the cell photosensitive and able to cause ion transport, cation or anion, in response to light. Nevertheless, although it is known that the retina is sensitive to very wide ranges of light intensities due to the adaptive nature of photoreceptors, light-gated ion channels or pumps may not be able to adapt and may therefore respond only to a narrow range of light intensities. If this is the case, such a limitation may be mitigated by use of image intensifiers and/or image converters known in the art. For example, a patient who has been treated by the above described method, may wear, image intensifiers/enhancers mounted, for example, on spectacles or the like.

By way of an example, an image intensifying device, such as those provided by Telesensory (http://www.telesensory.com), may be combined with a retinal scanning device (RSD) as developed by Microvision (http://www.microvision.com/milprod.html), to provide a head-worn apparatus capable of delivering a bright, intensified image directly to the retina of a patient with impaired vision (http://www.telesensory.com/home8.html). Briefly, a RSD projects images onto the retina such that an individual can view a large, full-motion image without the need for additional screens or monitors. Thus, by projecting an intensified image directly to the retina of an individual with impaired vision, it may be possible to improve vision in those considered to be blind.

In case of expressing the light-gated ion channel or pump in retinal bipolar or ganglion cells some aspects of the network processing capabilities of the retina can be lost. For example horizontal cell mediated lateral inhibition can be lost if light activates bipolar or ganglion cells. In these cases a retina like processor (D. Balya and B. Roska: "Retina model with real time implementation", International Symposium on Circuits and Systems ISCAS 2005, Kobe, Japan, May, pp. 5222-5225, also see http://www.anafocus.com/and http://www.eutecus.com/) can be combined with the Microvision system.

If the light-gated ion channel or pump is expressed in photoreceptors as mentioned before the polarity of light response in photoreceptors can inverse. That can be corrected with inverting the polarity of the projected image: dark pixels becoming light and light pixels becoming dark.

These and other aspects of the present invention should be apparent to those skilled in the art, from the teachings herein.

For convenience, the meaning of certain terms and phrases employed in the specification, examples, and appended claims are also provided below.

The singular forms "a," "an," and "the" include plural reference unless the context clearly dictates otherwise.

The "Archaea" are a group of prokaryotic and single-celled microorganisms. In this they are similar to bacteria but these two groups evolved differently, and are classified as different domains in the three-domain system. Originally these organisms were named archaebacteria. Although there is still uncertainty in the phylogeny, Archaea, Eukaryota and Bacteria were introduced as the fundamental classifications in the three-domain system by Carl Woese in 1977. As prokaryotes, archaea are also classified in kingdom Monera in the traditional five-kingdom Linnaean taxonomy. While their prokaryotic cell structure is similar to bacteria, the genes of Archaea and several of their metabolic pathways are more closely related to those of eukaryotes. One way to account for this is to group archaeans and eukaryotes together in the clade Neomura, which might have arisen from gram-positive bacteria. On the other hand, other studies have suggested that Archaea may instead be the most ancient lineage in the world, with bacteria and eukaryotes diverging from this group. Archaea were originally described in extreme environments, but have since been found in all habitats and may contribute up to 20% of total biomass. These cells are particularly common in the oceans, and the archaea in plankton may be one of the most abundant groups of organisms on the planet. A single individual or species from this domain is called an archaeon (sometimes spelled "archeon") while the adjectival form is archaeal or archaean.

"Halorhodopsin" is a light-driven ion pump, specific for chloride ions, and found in phylogenetically ancient "bacteria" (archaea), known as halobacteria. It is a seven-transmembrane protein of the retinylidene protein family, homologous to the light-driven proton pump bacteriorhodopsin, and similar in tertiary structure (but not primary sequence structure) to vertebrate rhodopsins, the pigments that sense light in the retina. Halorhodopsin also shares sequence similarity to channelrhodopsin, a light-driven ion channel. Halorhodopsin contains the essential light-isomerizable vitamin A derivative all-trans-retinal. Halorhodopsin is one of the few membrane proteins whose crystal structure is known. Halorhodopsin isoforms can be found in multiple species of halobacteria, including *H. salinarum*, and *N. pharaonis*. Much ongoing research is exploring these differences, and using them to parse apart the photocycle and pump properties. After bacteriorhodopsin, halorhodopsin may be the best type I (microbial) opsin studied. Peak absorbance of the halorhodopsin retinal complex is about 570 nm. Recently, halorhodopsin has become a tool in optogenetics. Just as the blue-light activated ion channel channelrhodopsin-2 opens up the ability to activate excitable cells (such as neurons, muscle cells, pancreatic cells, and immune cells) with brief pulses of blue light, halorhodopsin opens up the ability to silence excitable cells with brief pulses of yellow light. Thus halorhodopsin and channelrhodopsin together enable multiple-color optical activation, silencing, and desynchronization of neural activity, creating a powerful neuroengineering toolbox.

"Polynucleotide" and "nucleic acid", used interchangeably herein, refer to polymeric forms of nucleotides of any length, either ribonucleotides or deoxyribonucleotides. Thus, these terms include, but are not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases. These terms further include, but are not limited to, mRNA or cDNA that comprise intronic sequences. The backbone of the polynucleotide can comprise sugars and phosphate groups (as may typically be found in RNA or DNA), or modified or substituted sugar or phosphate groups. Alternatively, the backbone of the polynucleotide can comprise a polymer of synthetic subunits such as phosphoramidites and thus can be an oligodeoxynucleoside phosphoramidate or a mixed phosphoramidate-phosphodiester oligomer. A polynucleotide may comprise modified nucleotides, such as methylated nucleotides and nucleotide analogs, uracyl, other sugars, and linking groups such as fluoroibose and thioate, and nucleotide branches. The sequence of nucleotides may be interrupted by non-nucleotide components. A polynucleotide may be further modified after polymerization, such as by conjugation with a labeling component. Other types of modifications included in this definition are caps, substitution of one or more of the naturally occurring nucleotides with an analog, and introduction of means for attaching the polynucleotide to proteins, metal ions, labeling components, other polynucleotides, or a solid support. The term "polynucleotide" also encompasses peptidic nucleic acids, PNA and LNA. Polynucleotides may further comprise genomic DNA, cDNA, or DNA-RNA hybrids.

"Sequence Identity" refers to a degree of similarity or complementarity. There may be partial identity or complete identity. A partially complementary sequence is one that at least partially inhibits an identical sequence from hybridizing to a target polynucleotide; it is referred to using the functional term "substantially identical." The inhibition of hybridization of the completely complementary sequence to the target sequence may be examined using a hybridization assay (Southern or Northern blot, solution hybridization and the like) under conditions of low stringency. A substantially identical sequence or probe will compete for and inhibit the binding (i.e., the hybridization) of a completely identical sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarities (e.g., less than about 30% identity); in the absence of non-specific binding, the probe will not hybridize to the second non-complementary target sequence.

Another way of viewing sequence identity in the context to two nucleic acid or polypeptide sequences includes reference to residues in the two sequences that are the same when aligned for maximum correspondence over a specified region. As used herein, percentage of sequence identity means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity.

"Gene" refers to a polynucleotide sequence that comprises control and coding sequences necessary for the production of a polypeptide or precursor. The polypeptide can be encoded by a full length coding sequence or by any portion of the coding sequence. A gene may constitute an uninterrupted coding sequence or it may include one or more introns, bound by the appropriate splice junctions. Moreover, a gene may contain one or more modifications in either the coding or the untranslated regions that could affect the biological activity or the chemical structure of the expression product, the rate of expression, or the manner of expression control. Such modifications include, but are not limited to, mutations, insertions, deletions, and substitutions of one or more nucleotides. In this regard, such modified genes may be referred to as "variants" of the "native" gene.

"Expression" generally refers to the process by which a polynucleotide sequence undergoes successful transcription and translation such that detectable levels of the amino acid sequence or protein are expressed. In certain contexts herein, expression refers to the production of mRNA. In other contexts, expression refers to the production of protein.

"Cell type" refers to a cell from a given source (e.g., tissue or organ) or a cell in a given state of differentiation, or a cell associated with a given pathology or genetic makeup.

"Polypeptide" and "protein", used interchangeably herein, refer to a polymeric form of amino acids of any length, which may include translated, untranslated, chemically modified, biochemically modified, and derivatized amino acids. A polypeptide or protein may be naturally occurring, recombinant, or synthetic, or any combination of these. Moreover, a polypeptide or protein may comprise a fragment of a naturally occurring protein or peptide. A polypeptide or protein may be a single molecule or may be a multi-molecular complex. In addition, such polypeptides or proteins may have modified peptide backbones. The terms include fusion proteins, including fusion proteins with a heterologous amino acid sequence, fusions with heterologous and homologous leader sequences, with or without N-terminal methionine residues, immunologically tagged proteins, and the like.

A "fragment of a protein" refers to a protein that is a portion of another protein. For example, fragments of proteins may comprise polypeptides obtained by digesting full-length protein isolated from cultured cells. In one embodiment, a protein fragment comprises at least about 6 amino acids. In another embodiment, the fragment comprises at least about 10 amino acids. In yet another embodiment, the protein fragment comprises at least about 16 amino acids.

An "expression product" or "gene product" is a biomolecule, such as a protein or mRNA, that is produced when a gene in an organism is transcribed or translated or post-translationally modified.

"Host cell" refers to a microorganism, a prokaryotic cell, a eukaryotic cell or cell line cultured as a unicellular entity that may be, or has been, used as a recipient for a recombinant vector or other transfer of polynucleotides, and includes the progeny of the original cell that has been transfected. The progeny of a single cell may not necessarily be completely identical in morphology or in genomic or total DNA complement as the original parent due to natural, accidental, or deliberate mutation.

The term "functional equivalent" is intended to include the "fragments", "mutants", "derivatives", "alleles", "hybrids", "variants", "analogs", or "chemical derivatives" of the native gene or virus.

"Isolated" refers to a polynucleotide, a polypeptide, an immunoglobulin, a virus or a host cell that is in an environment different from that in which the polynucleotide, the polypeptide, the immunoglobulin, the virus or the host cell naturally occurs.

"Substantially purified" refers to a compound that is removed from its natural environment and is at least about 60% free, at least about 65% free, at least about 70% free, at least about 75% free, at least about 80% free, at least about 83% free, at least about 85% free, at least about 88% free, at least about 90% free, at least about 91% free, at least about 92% free, at least about 93% free, at least about 94% free, at least about 95% free, at least about 96% free, at least about 97% free, at least about 98% free, at least about 99% free, at least about 99.9% free, or at least about 99.99% or more free from other components with which it is naturally associated.

"Diagnosis" and "diagnosing" generally includes a determination of a subject's susceptibility to a disease or disorder, a determination as to whether a subject is presently affected by a disease or disorder, a prognosis of a subject affected by a disease or disorder (e.g., identification of pre-metastatic or metastatic cancerous states, stages of cancer, or responsiveness of cancer to therapy), and therametrics (e.g., monitoring a subject's condition to provide information as to the effect or efficacy of therapy).

"Biological sample" encompasses a variety of sample types obtained from an organism that may be used in a diagnostic or monitoring assay. The term encompasses blood and other liquid samples of biological origin, solid tissue samples, such as a biopsy specimen, or tissue cultures or cells derived therefrom and the progeny thereof. The term specifically encompasses a clinical sample, and further includes cells in cell culture, cell supernatants, cell lysates, serum, plasma, urine, amniotic fluid, biological fluids, and tissue samples. The term also encompasses samples that have been manipulated in any way after procurement, such as treatment with reagents, solubilization, or enrichment for certain components.

"Individual", "subject", "host" and "patient", used interchangeably herein, refer to any mammalian subject for whom diagnosis, treatment, or therapy is desired. In one preferred embodiment, the individual, subject, host, or patient is a human. Other subjects may include, but are not limited to, cattle, horses, dogs, cats, guinea pigs, rabbits, rats, primates, and mice.

"Hybridization" refers to any process by which a polynucleotide sequence binds to a complementary sequence through base pairing. Hybridization conditions can be defined by, for example, the concentrations of salt or formamide in the prehybridization and hybridization solutions, or by the hybridization temperature, and are well known in the art. Hybridization can occur under conditions of various stringency.

"Stringent conditions" refers to conditions under which a probe may hybridize to its target polynucleotide sequence, but to no other sequences. Stringent conditions are sequence-dependent (e. g., longer sequences hybridize specifically at higher temperatures). Generally, stringent conditions are selected to be about 5° C. lower than the thermal melting point (Tm) for the specific sequence at a defined ionic strength and pH. The Tm is the temperature (under defined ionic strength, pH, and polynucleotide concentration) at which 50% of the probes complementary to the target sequence hybridize to the target sequence at equilibrium. Typically, stringent conditions will be those in which the salt concentration is at least about 0.01 to about 1.0 M sodium ion concentration (or other salts) at about pH 7.0 to about pH 8.3 and the temperature is at least about 30° C. for short probes (e. g., 10 to 50 nucleotides).

Stringent conditions may also be achieved with the addition of destabilizing agents, such as formamide.

"Biomolecule" includes polynucleotides and polypeptides.

"Biological activity" refers to the biological behavior and effects of a protein or peptide. The biological activity of a protein may be affected at the cellular level and the molecular level. For example, the biological activity of a protein may be affected by changes at the molecular level. For example, an antisense oligonucleotide may prevent translation of a particular mRNA, thereby inhibiting the biological activity of the protein encoded by the mRNA. In addition, an immunoglobulin may bind to a particular protein and inhibit that protein's biological activity.

"Oligonucleotide" refers to a polynucleotide sequence comprising, for example, from about 10 nucleotides (nt) to about 1000 nt. Oligonucleotides for use in the invention are for instance from about 15 nt to about 150 nt, for instance from about 150 nt to about 1000 nt in length. The oligonucleotide may be a naturally occurring oligonucleotide or a synthetic oligonucleotide.

"Modified oligonucleotide" and "Modified polynucleotide" refer to oligonucleotides or polynucleotides with one or more chemical modifications at the molecular level of the natural molecular structures of all or any of the bases, sugar moieties, internucleoside phosphate linkages, as well as to molecules having added substitutions or a combination of modifications at these sites. The internucleoside phosphate linkages may be phosphodiester, phosphotriester, phosphoramidate, siloxane, carbonate, carboxymethylester, acetamidate, carbamate, thioether, bridged phosphoramidate, bridged methylene phosphonate, phosphorothioate, methylphosphonate, phosphorodithioate, bridged phosphorothioate or sulfone internucleotide linkages, or 3'-3', 5'-3', or 5'-5' linkages, and combinations of such similar linkages. The phosphodiester linkage may be replaced with a substitute linkage, such as phosphorothioate, methylamino, methylphosphonate, phosphoramidate, and guanidine, and the ribose subunit of the polynucleotides may also be substituted (e. g., hexose phosphodiester; peptide nucleic acids). The modifications may be internal (single or repeated) or at the end (s) of the oligonucleotide molecule, and may include additions to the molecule of the internucleoside phosphate linkages, such as deoxyribose and phosphate modifications which cleave or crosslink to the opposite chains or to associated enzymes or other proteins. The terms "modified oligonucleotides" and "modified polynucleotides" also include oligonucleotides or polynucleotides comprising modifications to the sugar moieties (e. g., 3'-substituted ribonucleotides or deoxyribonucleotide monomers), any of which are bound together via 5' to 3' linkages.

"Biomolecular sequence" or "sequence" refers to all or a portion of a polynucleotide or polypeptide sequence.

The term "detectable" refers to a polynucleotide expression pattern which is detectable via the standard techniques of polymerase chain reaction (PCR), reverse transcriptase-(RT) PCR, differential display, and Northern analyses, which are well known to those of skill in the art. Similarly, polypeptide expression patterns may be "detected" via standard techniques including immunoassays such as Western blots.

A "target gene" refers to a polynucleotide, often derived from a biological sample, to which an oligonucleotide probe is designed to specifically hybridize. It is either the presence or absence of the target polynucleotide that is to be detected, or the amount of the target polynucleotide that is to be quantified. The target polynucleotide has a sequence that is complementary to the polynucleotide sequence of the corresponding probe directed to the target. The target polynucleotide may also refer to the specific subsequence of a larger polynucleotide to which the probe is directed or to the overall sequence (e.g., gene or mRNA) whose expression level it is desired to detect.

A "target protein" refers to a polypeptide, often derived from a biological sample, to which a protein-capture agent specifically hybridizes or binds. It is either the presence or absence of the target protein that is to be detected, or the amount of the target protein that is to be quantified. The target protein has a structure that is recognized by the corresponding protein-capture agent directed to the target. The target protein or amino acid may also refer to the specific substructure of a larger protein to which the protein-capture agent is directed or to the overall structure (e. g., gene or mRNA) whose expression level it is desired to detect.

"Complementary" refers to the topological compatibility or matching together of the interacting surfaces of a probe molecule and its target. The target and its probe can be described as complementary, and furthermore, the contact surface characteristics are complementary to each other. Hybridization or base pairing between nucleotides or nucleic acids, such as, for example, between the two strands of a double-stranded DNA molecule or between an oligonucleotide probe and a target are complementary.

"Label" refers to agents that are capable of providing a detectable signal, either directly or through interaction with one or more additional members of a signal producing system. Labels that are directly detectable and may find use in the invention include fluorescent labels. Specific fluorophores include fluorescein, rhodamine, BODIPY, cyanine dyes and the like.

The term "fusion protein" refers to a protein composed of two or more polypeptides that, although typically not joined in their native state, are joined by their respective amino and carboxyl termini through a peptide linkage to form a single continuous polypeptide. It is understood that the two or more polypeptide components can either be directly joined or indirectly joined through a peptide linker/spacer.

The term "normal physiological conditions" means conditions that are typical inside a living organism or a cell. Although some organs or organisms provide extreme conditions, the intra-organismal and intra-cellular environment normally varies around pH 7 (i.e., from pH 6.5 to pH 7.5), contains water as the predominant solvent, and exists at a temperature above 0° C. and below 50° C. The concentration of various salts depends on the organ, organism, cell, or cellular compartment used as a reference.

"BLAST" refers to Basic Local Alignment Search Tool, a technique for detecting ungapped sub-sequences that match a given query sequence.

"BLASTP" is a BLAST program that compares an amino acid query sequence against a protein sequence database. "BLASTX" is a BLAST program that compares the six-frame conceptual translation products of a nucleotide query sequence (both strands) against a protein sequence database.

A "cds" is used in a Gen Bank DNA sequence entry to refer to the coding sequence. A coding sequence is a sub-sequence of a DNA sequence that is surmised to encode a gene.

A "consensus" or "contig sequence", as understood herein, is a group of assembled overlapping sequences, particularly between sequences in one or more of the databases of the invention.

The nucleic acid molecules of the present invention can be produced by a virus harbouring a nucleic acid that encodes the relevant gene sequence. The virus may comprise elements capable of controlling and/or enhancing expression of the nucleic acid. The virus may be a recombinant virus. The recombinant virus may also include other functional elements. For instance, recombinant viruses can be designed such that the viruses will autonomously replicate in the target cell. In this case, elements that induce nucleic acid replication may be required in a recombinant virus. The recombinant virus may also comprise a promoter or regulator or enhancer to control expression of the nucleic acid as required. Tissue specific promoter/enhancer elements may be used to regulate expression of the nucleic acid in specific cell types. The promoter may be constitutive or inducible.

A "promoters" is a region of DNA that is generally located upstream (towards the 5' region) of the gene that is needed to be transcribed. The promoter permits the proper activation or repression of the gene which it controls. Examples of promoters which are suitable for the invention are the human rhodopsin promoter (Allocca et al., Novel AAV serotypes efficiently transduce murine photoreceptors, J Virol. (2007)), the human red opsin promoter (Nathan et al., Science. 1986 Apr. 11; 232(4747):193-202), the red cone opsin promoter, the arr3 promoter (Zhu, X. et al. Mouse cone arrestin gene characterization: promoter targets expression to cone photoreceptors. *FEBS Letters* 524, 116-122 (2002)) or the Grm6 promoter (Masu, M. et al. Specific deficit of the ON response in visual transmission by targeted disruption of the mGluR6 gene. *Cell* 80, 757-765 (1995)).

Contaminant components of its natural environment are materials that would interfere with the methods and compositions of the invention, and may include enzymes, hormones, and other proteinaceous or nonproteinaceous solutes. Ordinarily, an isolated agent will be prepared by at least one purification step. In one embodiment, the agent is purified to at least about 60%, at least about 65%, at least about 70%, at least about 75%, at least about 80%, at least about 85%, at least about 88%, at least about 90%, at least about 92%, at least about 95%, at least about 97%, at least about 98%, at least about 99%, at least about 99.9%, or at least about 99.99% by weight.

"Expressing" a protein in a cell means to ensure that the protein is present in the cell, e. g., for the purposes of a procedure of interest. In numerous embodiments, "expressing" a protein will comprise introducing a transgene into a cell comprising a polynucleotide encoding the protein, operably linked to a promoter, wherein the promoter is a constitutive promoter, or an inducible promoter where the conditions sufficient for induction are created, as well as a localization sequence. However, a cell that, e. g., naturally expresses a protein of interest, can be used without manipulation and is considered as "expressing" the protein.

A "fluorescent probe" refers to any compound with the ability to emit light of a certain wavelength when activated by light of another wavelength.

"Fluorescence" refers to any detectable characteristic of a fluorescent signal, including intensity, spectrum, wavelength, intracellular distribution, etc.

"Detecting" fluorescence refers to assessing the fluorescence of a cell using qualitative or quantitative methods. For instance, the fluorescence is determined using quantitative means, e. g., measuring the fluorescence intensity, spectrum, or intracellular distribution, allowing the statistical comparison of values obtained under different conditions. The level can also be determined using qualitative methods, such as the visual analysis and comparison by a human of multiple samples, e. g., samples detected using a fluorescent microscope or other optical detector (e. g., image analysis system, etc.) An "alteration" or "modulation" in fluorescence refers to any detectable difference in the intensity, intracellular distribution, spectrum, wavelength, or other aspect of fluorescence under a particular condition as compared to another condition. For example, an "alteration" or "modulation" is detected quantitatively, and the difference is a statistically significant difference. Any "alterations" or "modulations" in fluorescence can be detected using standard instrumentation, such as a fluorescent microscope, CCD, or any other fluorescent detector, and can be detected using an automated system, such as the integrated systems, or can reflect a subjective detection of an alteration by a human observer.

An assay performed in a "homogeneous format" means that the assay can be performed in a single container, with no manipulation or purification of any components being required to determine the result of the assay, e. g., a test agent can be added to an assay system and any effects directly measured. Often, such "homogeneous format" assays will comprise at least one component that is "quenched" or otherwise modified in the presence or absence of a test agent. ell.

Any of a number of cell types can be used in the present invention. For example, any eukaryotic cell, including plant, animal, and fungal cells can be used. In some embodiments, neurone will be used. As used herein, "cells" can include whole cells (untreated cells), permeabilized cells, isolated mitochondria, and proteoliposomes, e. g., proteoliposomes reconstituted with a UCP or another protein of interest. The care and maintenance of cells, including yeast cells, is well known to those of skill in the art and can be found in any of a variety of sources, such as Freshney (1994) Culture of Animal Cells. Manual of Basic Technique, Wiley-Liss, New York, Guthrie & Fink (1991), Guthrie and Fink, Guide to Yeast Genetics and Molecular Biology, Academic Press, Ausubel et al. (1999) Current Protocols in Molecular Biology, Greene Publishing Associates, and others.

Cells can be used at any of a wide range of densities, depending on the dye, the test agent, and the particular assay conditions. For instance, a density of about $OD_{600}$=0.01 to 1 is used, for example between about 0.05 and 0.5, e.g. about 0.1.

Methods for expressing heterologous proteins in cells are well known to those of skill in the art, and are described, e. g., in Ausubel (1999), Guthrie and Fink (1991), Sherman, et al. (1982) Vlethods ineast Genetics, Cold Spring Harbor Laboratories, Freshney, and others. Typically, in such embodiments, a polynucleotide encoding a heterologous protein of interest will be operably linked to an appropriate expression control sequence for the particular host cell in which the heterologous protein is to be expressed. Any of a large number of well-known promoters can be used in such method. The choice of the promoter will depend on the expression levels to be achieved and on the desired cellular specificity. Additional elements such as polyadenylation signals, 5' and 3' untranslated sequences, etc. are also described in well-known reference books.

In metazoan (animals having the body composed of cells differentiated into tissues and organs) cells, promoters and other elements for expressing heterologous proteins are commonly used and are well known to those of skill. See, e. g., Cruz & Patterson (1973) Tissue Culture, Academic Press; Meth. Enzymology 68 (1979), Academic Press; Freshney, 3rd Edition (1994) Culture of Animal Cells: A Manual of Basic Techniques, Wiley-Liss. Promoters and control sequences for such cells include, e. g., the commonly used early and late promoters from Simian Virus 40 (SV40), or other viral promoters such as those from polyoma, adenovirus 2, bovine papilloma virus, or avian sarcoma viruses, herpes virus family (e. g., cytomegalovirus, herpes simplex virus, or Epstein-Barr Virus), or immunoglobulin promoters and heat shock promoters (see, e. g. Sambrook, Ausubel, Meth. Enzymology Pouwells, et al., supra (1987)). In addition, regulated promoters, such as metallothionein, (i. e., MT-1 and MT-2), glucocorticoid, or antibiotic gene "switches" can be used. Enhancer regions of such promoters can also be used.

Expression cassettes are typically introduced into a vector that facilitates entry of the expression cassette into a host cell and maintenance of the expression cassette in the host cell. Such vectors are commonly used and are well know to those of skill in the art. Numerous such vectors are commercially available, e. g., from Invitrogen, Stratagene, Clontech, etc., and are described in numerous guides, such as Ausubel, Guthrie, Strathem, or Berger, all supra. Such vectors typically include promoters, polyadenylation signals, etc. in conjunction with multiple cloning sites, as well as additional elements such as origins of replication, selectable marker genes (e. g., LEU2, URA3, TRP 1, HIS3, GFP), centromeric sequences, etc.

For expression in mammalian cells, any of a number of vectors can be used, such as pSV2, pBC12BI, and p91023, as well as lytic virus vectors (e. g., vaccinia virus, adenovirus, baculovirus), episomal virus vectors (e. g., bovine papillomavirus), and retroviral vectors (e. g., murine retroviruses).

As used herein, the term "disorder" refers to an ailment, disease, illness, clinical condition, or pathological condition.

As used herein, the term "pharmaceutically acceptable carrier" refers to a carrier medium that does not interfere with the effectiveness of the biological activity of the active ingredient, is chemically inert, and is not toxic to the patient to whom it is administered.

As used herein, the term "pharmaceutically acceptable derivative" refers to any homolog, analog, or fragment of an agent, e.g. identified using a method of screening of the invention, that is relatively non-toxic to the subject.

The term "therapeutic agent" refers to any molecule, compound, or treatment, that assists in the prevention or treatment of disorders, or complications of disorders.

Compositions comprising such an agent formulated in a compatible pharmaceutical carrier may be prepared, packaged, and labeled for treatment.

If the complex is water-soluble, then it may be formulated in an appropriate buffer, for example, phosphate buffered saline or other physiologically compatible solutions.

Alternatively, if the resulting complex has poor solubility in aqueous solvents, then it may be formulated with a non-ionic surfactant such as Tween, or polyethylene glycol. Thus, the compounds and their physiologically acceptable solvates may be formulated for administration by inhalation or insufflation (either through the mouth or the nose) or oral, buccal, parenteral, rectal administration or, in the case of tumors, directly injected into a solid tumor.

For oral administration, the pharmaceutical preparation may be in liquid form, for example, solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e. g., almond oil, oily esters, or fractionated vegetable oils); and preservatives (e. g., methyl or propyl-p-hydroxybenzoates or sorbic acid). The pharmaceutical compositions may take the form of, for example, tablets or capsules prepared by conventional means with pharmaceutically acceptable excipients such as binding agents (e. g., pregelatinized maize starch, polyvinyl pyrrolidone or hydroxypropyl methylcellulose); fillers (e. g., lactose, microcrystalline cellulose or calcium hydrogen phosphate); lubricants (e. g., magnesium stearate, talc or silica); disintegrants (e. g., potato starch or sodium starch glycolate); or wetting agents (e. g., sodium lauryl sulphate). The tablets may be coated by methods well-known in the art.

Preparations for oral administration may be suitably formulated to give controlled release of the active compound.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e. g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e. g., gelatin for use in an inhaler or insufflator may be formulated containing a powder mix of the compound and a suitable powder base such as lactose or starch.

The compounds may be formulated for parenteral administration by injection, e. g., by bolus injection or continuous infusion. Formulations for injection may be presented in unit dosage form, e. g., in ampoules or in multi-dose containers, with an added preservative.

The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e. g., sterile pyrogen-free water, before use.

The compounds may also be formulated in rectal compositions such as suppositories or retention enemas, e. g., containing conventional suppository bases such as cocoa butter or other glycerides.

The compounds may also be formulated as a topical application, such as a cream or lotion.

In addition to the formulations described previously, the compounds may also be formulated as a depot preparation. Such long acting formulations may be administered by implantation (for example, subcutaneously or intramuscularly) or by intramuscular injection.

Thus, for example, the compounds may be formulated with suitable polymeric or hydrophobic materials (for example, as an emulsion in an acceptable oil) or ion exchange resins, or as sparingly soluble derivatives, for example, as a sparingly soluble salt. Liposomes and emulsions are well known examples of delivery vehicles or carriers for hydrophilic drugs.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The invention also provides kits for carrying out the therapeutic regimens of the invention. Such kits comprise in one or more containers therapeutically or prophylactically effective amounts of the compositions in pharmaceutically acceptable form.

The composition in a vial of a kit may be in the form of a pharmaceutically acceptable solution, e. g., in combination with sterile saline, dextrose solution, or buffered solution, or other pharmaceutically acceptable sterile fluid. Alternatively, the complex may be lyophilized or desiccated; in this instance, the kit optionally further comprises in a container a pharmaceutically acceptable solution (e. g., saline, dextrose solution, etc.), preferably sterile, to reconstitute the complex to form a solution for injection purposes.

In another embodiment, a kit further comprises a needle or syringe, preferably packaged in sterile form, for injecting the complex, and/or a packaged alcohol pad. Instructions are optionally included for administration of compositions by a clinician or by the patient.

In one embodiment, an isolated nucleic acid molecule comprising a nucleotide sequence coding for a hyperpolarizing light-gated ion channel or pump gene from an archeon, or for a light-active fragment of said gene, will be expressed, eventually together with a channelrohdopsin, e.g. channelrhodpsin-2 (ChR2), exclusively in ON-bipolar cells, whereas a cation-conducting channelrhodopsin, e.g. the vChR1 derived from Volvox carteri (Zhang et al., Red-shifted optogenetic excitation: a tool for fast neural control derived from Volvox carteri, Nat Neurosci. 2008 Apr. 23; doi:10.1038/nn.2120) will be expressed exclusively in OFF bipolar cells. Without wishing to be bound by theory, it is believed that this targeted expression of three neuromodulators will result in an excitation of the ON pathway by blue light (ChR2 component), and inhibition of said ON pathway by red light (NpHR component) whereas the OFF pathway will be excited by red light (vChR1 component). Hence, blue light would mimic light ON and red light would mimic light OFF. The advantage of this system is believed to be that the OFF bipolar cells would be directly excited (meaning depolarized) by vChR1. Without wishing to be bound by theory, it is believed that this combined and targeted expression of e.g. ChR2, NpHR and vChR1 might improve the spectrum of artificial photoreceptors after photoreceptor loss in quantity (more and different bipolar cells, ON and OFF) and might establish bichromatic vision (blue=white and red=black).

In addition, it is believed that the combination of ChR2/NpHR in ON bipolar cells might help to establish a sharp boundary between these two types of artificial photoreceptors since it could shut down the ON signal when red light is on and the OFF pathway will be turned on. As explained herein, the Grm6 promoter (Masu, M. et al. Specific deficit of the ON response in visual transmission by targeted disruption of the mGluR6 gene. Cell 80, 757-765 (1995).) is an exemplary promoter that could be used to drive expression of ChR2/NpHR in ON bipolar cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the present specification, including definitions, will control. In addition, the materials, methods, and examples are illustrative only and not intended to be limiting.

EXAMPLES

Genetic Approaches:

The present inventors expressed the red-light-sensitive chloride pump NpHR (Zhang et al., Multimodal fast optical interrogation of neural circuitry, Nature Vo1466 (2007)) in photoreceptors of C57BL/6 mice using adeno associated virus vector, AAV2/7 (Allocca et al., Novel AAV serotypes efficiently transduce murine photoreceptors, J Virol. (2007)), mediated gene transfer. NpHR was driven from the human rhodopsin promoter.

Detection of NpHR in Infected Retinae:

AAV2/7-Rho-NpHR-EYFP (5.35E+12 particles/ml) was injected subretinally into adult C57BL/6 mice. Retinae of infected animals were prepared at different time points post injection. These retinae were antibody-stained for EYFP to label NpHR-expressing cells and with DAPI to visualize all cells in the outer nuclear layer (ONL). Confocal microscopy recordings were performed and these were analyzed by using Bitplane's Imaris (5.7.2) software.

The quantification of infected photoreceptors was done by counting NpHR-expressing cells relative to DAPI-labeled cells in confocal slices.

Figure 2:
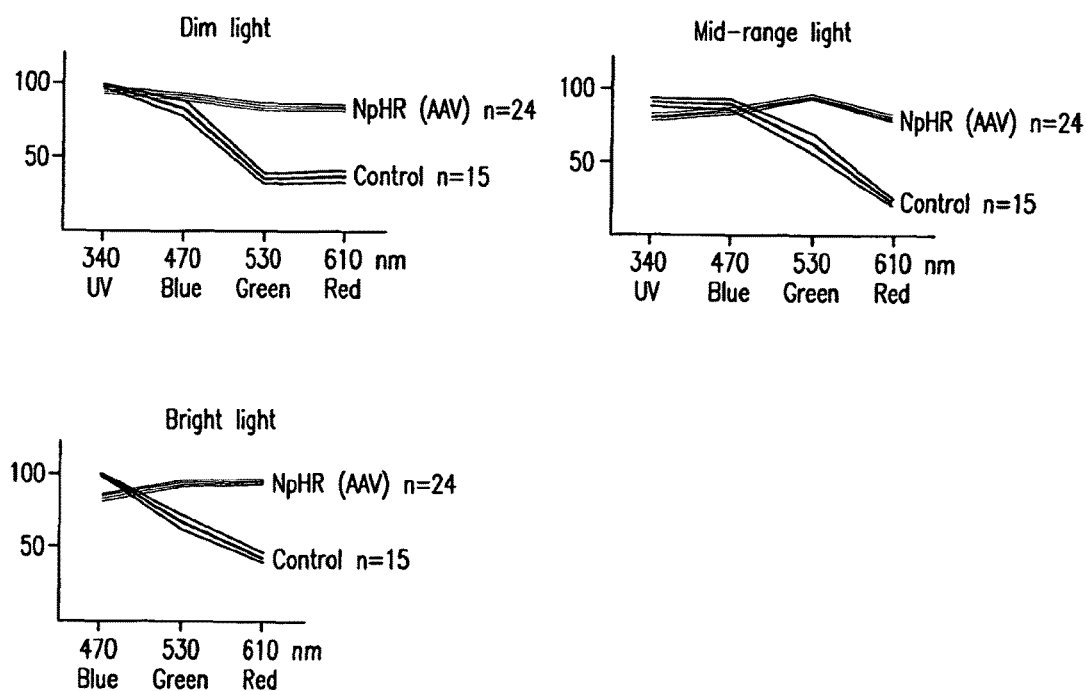
FIG. 2: Spectral tuning curve (mean total number of spikes during light ON normalized to each cell and light level) of AAV-NpHR-infected retinae (grey) and untreated control retinae (black) of mice (please note that mice do not normally possess a red-light-sensitive receptor).

Multielectrode Array Recordings of AAV-Infected Retinas:

The photoreceptors of AAV-infected retinae were stimulated by using light of defined wavelengths and intensities. The spiking output of ganglion cells was recorded by MEA. The spectral tuning curve of AAV infected retinas showed significantly higher light sensitivity at longer wavelengths compared to control untreated retinas (FIG. 2).

Results:

With these experiments, the present inventors were able to show that AAV2/7 in combination with the human rhodopsin promoter is an excellent tool for the delivery of NpHR into photoreceptors. The onset of NpHR expression was very fast (6 days post injection) and stable over a long period. As reported before, AAV2/7 particles penetrate the whole outer nuclear layer independent of injection site and ONL depth (Li et al., Cone-specific expression using a human red opsin promoter in recombinant AAV, Vision Research 48 (2008)). AAV infections at PO were less effective and likely rod restricted. The red-light-sensitive chloride pump NpHR was found to be functional in retinal explants. The obtained results demonstrate that NpHR can modulate photoreceptor activity towards higher wavelengths (Jacobs et al., Emergence of novel color vision in mice engineered to express a human cone photopigment, Science, VOL 315 (2007)).

The invention claimed is:

1. An isolated nucleic acid molecule comprising a nucleotide sequence coding in a 5' to 3' orientation for:
    (a) a human rhodopsin promoter or human red opsin promoter; and
    (b) a *Natronomas pharaonis* (NpHR) hyperpolarizing light-gated ion channel or pump gene or a light-active fragment of the gene.

2. The isolated nucleic acid molecule of claim 1 further comprising:
    (c) a nucleotide sequence coding for a depolarizing light-gated ion channel or pump gene.

3. The isolated nucleic acid molecule of claim 2, wherein the depolarizing light-gated ion channel or pump gene is a channelrhodopsin.

4. The isolated nucleic acid molecule of claim 2, wherein the hyperpolarizing light-gated ion channel or pump and the depolarizing light-gated ion channel or pump are encoded to form a fusion protein.

5. The isolated nucleic acid molecule of claim 2, wherein expression of the gene encoding the depolarizing light-gated ion channel or pump is under the control of a human rhodopsin promoter or human red opsin promoter.

6. A recombinant vector comprising the nucleic acid molecule of claim 1.

7. An isolated host cell comprising the vector of claim 6.

8. The isolated nucleic acid molecule of claim 1, wherein the promoter is a human rhodopsin promoter.

9. The isolated nucleic acid molecule of claim 1, wherein the promoter is a human red opsin promoter.

10. The isolated nucleic acid molecule of claim 3, wherein the channelrhodopsin is channelrhodopsin-2.

11. A method of treating or ameliorating blindness in a subject, the method comprising:
    administering to a retinal cell of the subject an isolated nucleic acid molecule comprising a nucleotide sequence coding in a 5' to 3' orientation for:
    (a) a human rhodopsin promoter or human red opsin promoter operably linked to; and
    (b) a *Natronomas pharaonis* (NpHR) hyperpolarizing light-gated ion channel or pump gene or a light-active fragment of the gene,
    thereby treating or ameliorating blindness in the subject.

12. The method of claim 11, wherein the retinal cell is a cone cell.

13. The method of claim 11, wherein the retinal cell is a rod cell.

14. The method of claim 11 further comprising simultaneously or sequentially administering a depolarizing light-gated ion channel or pump gene.

15. The method of claim 14, wherein the depolarizing light-gated ion channel or pump gene is a channelrhodopsin.

16. The method of claim 15, wherein the channelrhodopsin is channelrhodopsin-2.

17. The method of claim 14, wherein the depolarizing light-gated ion channel or pump gene is under the control of a human rhodopsin promoter.

18. The method of claim 14, wherein the depolarizing light-gated ion channel or pump gene is under the control of a human red opsin promoter.

* * * * *